US006558687B2

(12) United States Patent
Cederholm-Williams et al.

(10) Patent No.: US 6,558,687 B2
(45) Date of Patent: May 6, 2003

(54) FIBRIN POLYMER STRUCTURE

(75) Inventors: Stewart A. Cederholm-Williams, Oxford (GB); Julian M. Marshall, Oxford (GB); Jose L. Velada, Manchester (GB); Derek A. Hollingsbee, Neston (GB)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/997,544

(22) Filed: Nov. 29, 2001

(65) Prior Publication Data

US 2002/0150611 A1 Oct. 17, 2002

Related U.S. Application Data

(62) Division of application No. 09/585,500, filed on Jun. 1, 2000, now Pat. No. 6,462,018
(60) Provisional application No. 60/136,902, filed on Jun. 1, 1999.

(51) Int. Cl.$^7$ .......................... A61L 24/10; A61L 26/00; A61L 31/04; A61L 31/14; A61K 9/70
(52) U.S. Cl. ........................ 424/423; 530/380; 530/381; 530/382; 530/402; 514/2; 514/8; 514/12; 428/473; 428/478.2; 424/428; 424/426
(58) Field of Search ................................. 530/382, 380, 530/381, 402; 514/8, 2, 12; 428/473, 478.2; 424/423, 424, 426

(56) References Cited

U.S. PATENT DOCUMENTS

| 5,750,657 A | | 5/1998 | Edwardson et al. | |
|---|---|---|---|---|
| 6,121,422 A | * | 9/2000 | Zimmerman et al. | ....... 530/381 |
| 6,206,905 B1 | * | 3/2001 | Holm et al. | ................. 606/213 |

FOREIGN PATENT DOCUMENTS

| EP | 0592242 A | 4/1994 |
|---|---|---|
| WO | WO9720585 A | 6/1997 |
| WO | WO9802098 A | 1/1998 |
| WO | WO9820931 A | 5/1998 |

* cited by examiner

*Primary Examiner*—Frederick Krass
(74) *Attorney, Agent, or Firm*—John M. Kilcoyne

(57) ABSTRACT

In accordance with the present invention a novel fibrin polymer structure is disclosed. The novel fibrin polymer structure useful, for example, as a surgical sealant, is comprised of a plurality of discrete, droplets of polymerizing or polymerized fibrin each encapsulated by a "skin" of fibrin polymer. These fibrin-skin encapsulated droplets are applied so as to be built up one upon the other, layer by layer, to form an integral sealant structure. The cumulative effect of the encapsulating skins of those droplets which form the sealant surface is a surface skin which unexpectedly resists cell penetration but enhances cell migration across the surface. The sealant structure of the present invention can be prepared by spray delivery of fibrin polymer forming materials wherein the time required for the materials to commence polymerizing after mixing is less than or equal to the transit time of said materials from the applicator tip to the target surface.

11 Claims, 12 Drawing Sheets

FIBRIN POLYMER STRUCTURE

Divisional of prior application Ser. No. 09/585,500, filed Jun. 1, 2000 and now U.S. Pat. No. 6,462,018.

FIELD OF THE INVENTION

This application also claims benefit of Provisional Application No. 60/136/902 filed Jun. 1, 1999.

This invention related to a novel fibrin polymer structure and is more particularly directed to enhanced fibrin sealants and methods for their preparation.

BACKGROUND OF THE INVENTION

One mechanism for hemostasis in a mammal is the formation of a blood clot. Clot formation in humans, for example, occurs by means of a complex cascade of reactions with the final steps being the conversion of fibrinogen (a monomer) in the blood by thrombin, calcium ions and activated factor XIII to ultimately form a crosslinked fibrin II polymer.

A fibrin sealant is a biological material whose effect imitates the final stages of coagulation. The prior art is replete with disclosures of two component fibrin sealant systems which co-administer fibrinogen and thrombin, typically in the presence of calcium ions and factor XIIIa, to form a fibrin clot or sealant at a desired surgical site. In prior art sealants the two sealant-forming components are co-applied or co-sprayed as liquids. The fibrinogen and thrombin interact at the surface or desired sealant site to form the fibrin polymer. Many different methods and devices have been proposed to enhance the uniformity of the mixing and interaction of the fibrinogen and thrombin components in order to enhance the uniformity of the resultant sealant. A device and method are described in WO 98/02098 which provide for a uniform mixing of the fibrinogen and thrombin components at the target surface to provide a uniform, substantially homogenous fibrin polymer sealant.

It is understood in the area of fibrin sealants that there is a "lag" time for polymerization to commence. The thrombin needs to act upon the fibrinogen to catalyze the cleavage of fibrinopeptide A and eventually fibrinopeptide B thrombin needs to act upon the fibrinogen to catalyze the cleavage of fibrinopeptide A and eventually fibrinopeptide B from fibrinogen before the resulting fibrin can begin to polymerize. In fact, fibrinogen itself is believed to inhibit the polymerization of fibrin such that polymerization will not begin until at least 25% of the fibrinogen has been converted to fibrin I monomer, i.e., by cleavage of fibrinopeptide A. In these prior art sealants, although the efficiency of mixing and spraying may enhance the overall uniformity of the fibrin polymer formed, the characteristics of the sealant structure itself, i.e., fibril size and density, pore size and density, are primarily dependent upon concentrations of fibrinogen and/or thrombin.

SUMMARY OF THE INVENTION

Figure 1:
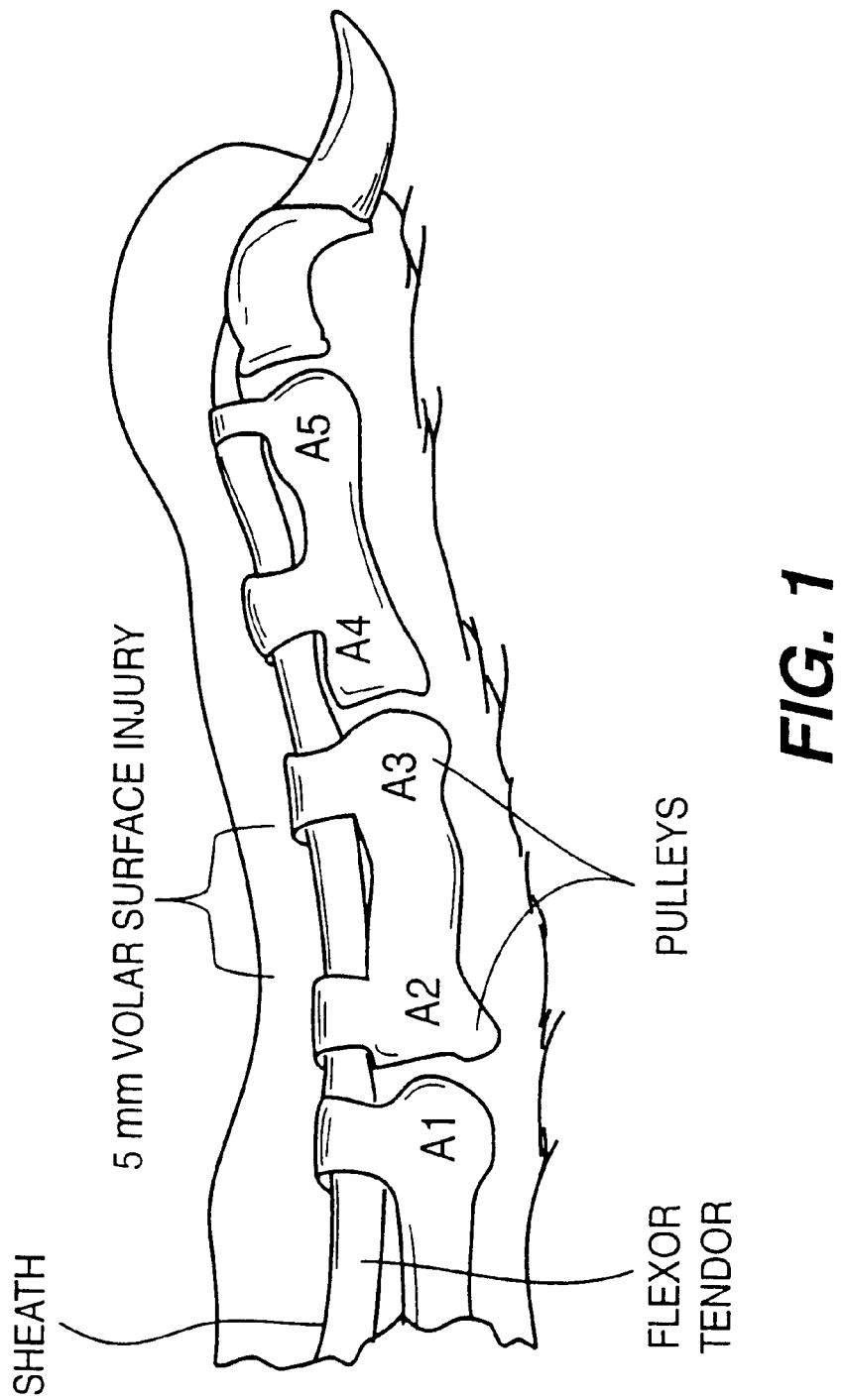
FIG. 1 Illustrates a rabbit paw flexor tendon per the experiments of Example 2.
Figure 2:
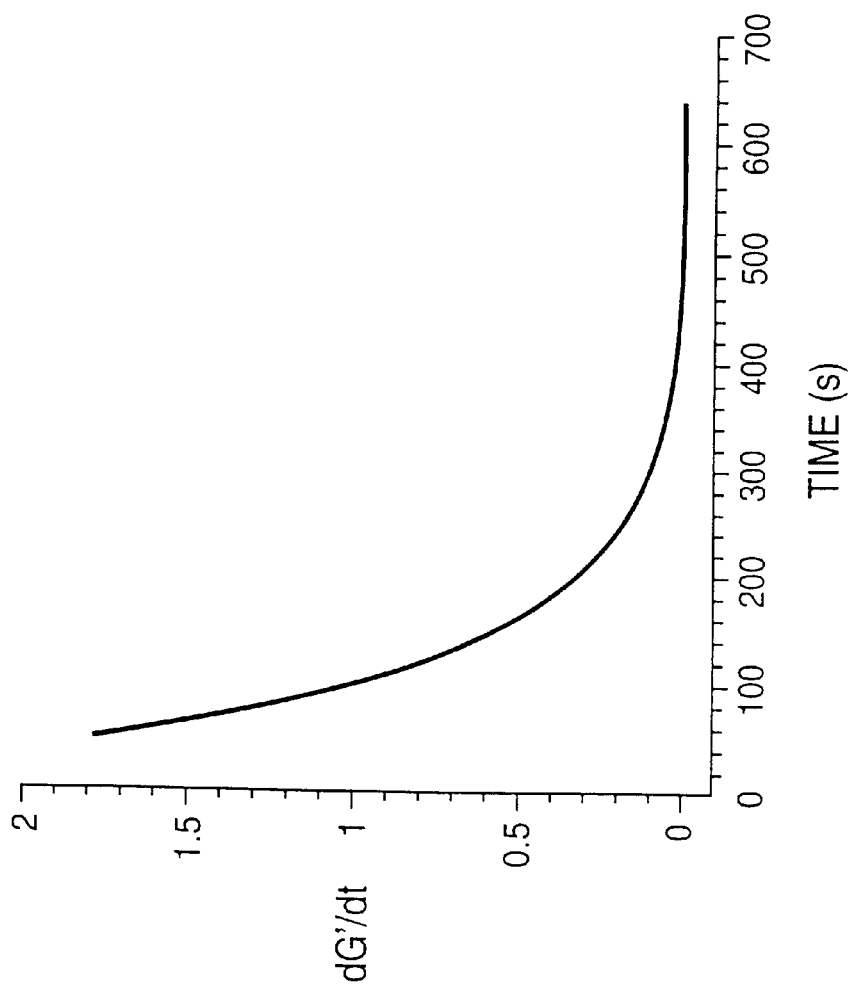
FIG. 2 Is a graph showing variation of dG'/dt with time per Example 2.

In accordance with the present invention a novel fibrin polymer structure is disclosed. The novel fibrin polymer structure useful, for example, as a surgical sealant, is comprised of a plurality of discrete, droplets of polymerizing or polymerized fibrin each encapsulated by a "skin" of fibrin polymer. These fibrin-skin encapsulated droplets are applied so as to be built up one upon the other, layer by layer, to form an integral sealant structure. The cumulative effect of the encapsulating skins of those droplets which form the sealant surface is a surface skin which unexpectedly resists cell penetration but enhances cell migration across the surface. The sealant structure of the present invention can be prepared by spray delivery of fibrin polymer forming materials wherein the time required for the materials to commence polymerizing after mixing is less than or equal to the transit time of said materials from the applicator tip to the target surface.

DETAILED DESCRIPTION OF PREFERRED EMBODIMENTS

For the purpose of the subject invention, the following definitions are utilized:

Fibrin—Fibrin means any form of fibrin. Nonlimiting examples of fibrin include fibrin I, fibrin II and des BB fibrin. The fibrin can be in monomeric form or polymeric form, wherein the polymeric form is either noncrosslinked or crosslinked.

Fibrin Monomer-Fibrin monomer includes any form of fibrin, e.g., fibrin I, fibrin II and des BB fibrin wherein the fibrin is in monomeric form or oligomeric form that can be solubilized in the composition comprising fibrin monomer and wherein the fibrin monomer can be converted to fibrin polymer.

Fibrin Polymer-Fibrin Polymer includes any form of fibrin, e.g., fibrin I, fibrin II and des BB fibrin wherein said fibrin is in polymeric form, either noncrosslinked or crosslinked.

Noncrosslinked Fibrin-Noncrosslinked fibrin includes any form of fibrin, e.g., fibrin I, fibrin II and des BB fibrin wherein said fibrin is noncrosslinked and can be converted to crosslinked fibrin. The noncrosslinked fibrin can be fibrin monomer or noncrosslinked fibrin polymer.

Crosslinked Fibrin-Crosslinked fibrin includes any form of fibrin, e.g., fibrin I, fibrin II and des BB fibrin wherein the fibrin is a fibrin polymer that is crosslinked.

The unique fibrin polymer structure which has been discovered provides many distinct advantages over prior art fibrin sealants. The fibrin polymer structure is generally a film or layer and is, in a preferred embodiment, a fibrin sealant. It will be referred to throughout this application as a fibrin sealant or sealant structure, but it should be understood that it could be a fibrin polymer film layer or laminate of layers for any other purpose as well. The sealant structure of the present invention is the result of a plurality of discrete, skin-encapsulated, polymerized or partially polymerized droplets applied to a desired site so as to build up an integral sealant of desired thickness. The resulting sealant is a coherent structure which upon close examination still retains visual evidence (by electron microscopy) of the plurality of discrete droplets which have been built up, one upon the other, layer by layer. Despite the fact that the present structure is built up of discrete polymerized or semi-polymerized droplets, unexpectedly, the cumulative effect of the plurality of encapsulating skins which individually encapsulate the droplets, but together form the outer surface of the sealant structure, is that of a "barrier" to cell penetration, although it is not known if the present sealant structure is a physical barrier or whether it just resists cellular penetration. Further unexpected, is that cell migration across the outer surface of the sealant structure is greatly enhanced.

The discrete droplets which form the sealant structure of the present invention are the result of a number of factors. The droplets are typically generated by a spray applicator capable of producing droplets from a liquid source. Beyond this, however, the present inventors have discovered that it is critical for the fibrin-polymer-forming material being sprayed to be capable of commencing polymerization prior to hitting its target. That is, the droplets begin to polymerize in the short journey from the applicator tip to the target. Depending upon the polymerization rate of the precursor materials used to form the fibrin polymer film and upon the droplet size resulting from the spray method, some, most or substantially all of the droplets are able to retain some of their "individuality" as a droplet, while at the same time accumulating to form an integral sealant structure. Besides, but possibly related to, the fact that the droplets are polymerizing, it has been observed that a thin skin encapsulates each polymerizing droplet. Although the origin of this skin is not completely understood, it is believed to be a result of the air/droplet surface interaction which occurs during spray delivery; possibly a partial drying phenomenon. The skin is a highly concentrated fibrin layer made up of thin fibrils which are 10–20 times thinner than fibrin fibrils formed in the center of each polymerized droplet. The encapsulating fibrin skin is analogous to the cell membrane of a cell. Although the skin is fibrin polymer, its interaction with the air during spray delivery has altered this encapsulating region of fibrin polymer to create a thin barrier layer around each droplet which is impervious to, or at least resists, cell penetration. Thus, the droplets hitting the target surface and forming the sealant are polymerized, or polymerizing, solutions of fibrin-polymer-forming material encapsulated with a fibrin polymer skin somehow modified by interaction with air to be impenetrable by cells. In fact, sealants of various concentrations have been produced which yield various pore sizes and fibril sizes within the inside of the sealant structure with no variation in penetrability by cells because of the "surface skin" of the present sealant comprised of the encapsulating skins of the droplets at the surface of the present sealant structure.

This unique fibrin skin is, itself, considered to be a part of the present invention since it is contemplated that the skin even without the droplet can be prepared. The film skin ends up being a highly concentrated fibrin polymer film which can be formed from a relatively low concentration precursor. Indeed, using this air-interaction process films of varying concentration can be made and laminated into a multilayer structure. In this way, a wound or surgical site would "see" layers of varying fibrin concentration during the fibrin degradation process. Fibrin sealants made in this manner could be tailored for specific concentration according to the stage of wound healing.

Again, it is important to note that in utilizing a fibrin monomer solution to form this high fibrin concentration skin, the fact that fibrinopeptide A has already been cleaved allows for the nonenzymic polymerization of the monomer to form the polymer. This skin is distinct from the outside layer of prior art sealants because the rate of polymerization is at least an order of magnitude faster than enzymic polymerization utilized in fibrinogen/thrombin system.

When the sealant structure of the present invention is formed by spraying, depending upon the spray application parameters, the droplets may flatten upon impact with the desired site or the droplets already applied thereto. Thus, the droplets making up the present sealant structure may be more in the shape of plates. These plates or droplets are sticky which allows the plurality of plates or droplets to form an integral structure. It also provides that the structure will, itself, be adherent. It is believed that the tensile strength and elasticity of the sealant structure of the present invention are attributable not only to the inherent qualities of the fibrin polymer formed within each plate or droplet, but are also due to the likelihood that the plates or droplets slide or move in relation to one another upon stress. Accordingly, tensile strength and elasticity of the present sealant structure are significantly enhanced over prior art sealants.

This structure is not accomplished with prior art sealant methods because prior art sealants as mentioned above, go through enzymic polymerization which is much slower than the present system and the polymerization/air interaction provides significantly different results. Also, when compared to the presently preferred spray techniques, the prior art sealants are designed to be applied to, and impact, the target surface as liquid drops which mix at the target surface to form a homogenous fibrin polymer. That is, prior art sealant methods rely upon polymerization at the target following liquid application. By the time polymerization has started with prior art sealant methods, there are no more droplets. The process of interacting small, polymerizing droplets with air during spray delivery does not occur in prior art sealant methods. In order to provide the novel sealant structure to prior art fibrinogen/thrombin sealant methods, the reaction time of the thrombin upon the fibrinogen would need to be increased enormously so that co-administration of fibrinogen and thrombin solutions would result in polymerization of fibrin droplets in-flight which could then interact with the air, also in-flight.

As mentioned, a preferred method of preparing the novel fibrin polymer sealant structure of the present invention involves the spray application of a fibrin monomer solution although any system which can initiate polymerization "in flight" during spray application of fibrin sealants would be considered part of the present invention. Further descriptions of this invention will refer to the application of a fibrin monomer (as opposed to fibrinogen and thrombin) to form this novel structure, unless otherwise noted. It has now been found that fibrin monomer solutions which retain the fibrin monomer in a nondynamic state, polymerize extremely rapidly when the nondynamic conditions are reversed. In fact, as mentioned above it is now understood in comparable spray application methods that nondynamic fibrin monomer, when converted to dynamic fibrin monomer, will polymerize 10 times faster than fibrinogen and thrombin co-applied according to prior art methods. Methods and compositions utilizing fibrin monomer to prepare fibrin polymers useful, e.g., as fibrin sealants are known and are described, for example, in U.S. Pat. No. 5,750,657, U.S. Pat. No. 5,770, 194, U.S. Pat. No. 5,773,418, U.S. Pat. No. 5,804,428. In a preferred embodiment in those patents the fibrin monomer can be retained in a nondynamic state by keeping the monomer at low pH. This low pH solution can be co-applied from a spray applicator with a buffer solution which raises the pH to reverse the nondynamic condition and promote polymerization of the fibrin.

It should be understood that the fibrin sealant comprising a plurality of encapsulated, polymerized or polymerizing fibrin-polymer-forming material, as described, above refers to the structure immediately upon application, i.e., the encapsulating skin of fibrin polymer is present immediately, and for applications requiring a barrier to cell penetration no "curing" period is required. The "polymerized or polymerizing fibrin-polymer-forming material" within the encapsulating skin of each droplet does, however, undergo changes over time. In particular, it has been found the fibrin-polymer-forming solution within the droplet forms a gel-like polymer within about 20–300 seconds of application to the desired site. Thus, a few minutes after application the "polymerizing" center of each droplet is polymerized. Further, when conditions for crosslinking are provided, crosslinking of the fibrin alpha and/or gamma chains will occur.

Since the initiation of fibrin polymerization and encapsulating skin formation must occur in flight during spray delivery, the delivery rate or the rate of polymerization should be controlled so that the in flight time is greater than, or equal to, the time needed for polymerization to commence. That is, the delivery rate and/or the rate of polymerization must be selected to allow encapsulation before droplet impact. WO 98/20931 discloses a spray applicator suitable for spraying surgical sealant components, e.g., fibrin monomer and an accompanying polymerizing solution. WO 98/20931 suggests that the combined solution flow rates (fibrin monomer+polymerizing pH 10 buffer) can have, for example, between 0.7 ml/min and 2.8 ml/min. Accompanying gas spray is suggested to be 1.25 liters/minute and below, for example, between about 500 ml/min and 800 ml/min depending upon the desired spray characteristics.

At any given set of spray parameters, the polymerization rate can be changed by changing concentrations of fibrin monomer, the higher concentrations providing the faster polymerization rates.

Conversely, lower concentrations provide slower polymerization rates. Therefore, at a given set of spray parameters there will exist a threshold polymerization rate, or concentration, below which polymerization and encapsulation of droplets will not occur in flight. For fibrin monomer compositions it has been found that at about 15 mg/ml of fibrin and above, the novel sealant structure formed of discrete fibrin encapsulated droplets is achieved. For example, a typical spray distance can be about 5 centimeters providing that, at the flow rates described above, e.g., about 0;7 ml/minute of combined liquids (fibrin monomer+ polymerizing buffer), the sprayed droplets commence polymerization in a timeframe on the order of <100 milliseconds. Complete polymerization takes place over the next 60–300 seconds with optional crosslinking to follow.

Further, between about 10 and 15 mg/ml of fibrin monomer, many, but not all, of the droplets remain intact and are encapsulated upon target impact. Accordingly, other of the droplets are still liquid or have insufficient skin formation such that upon impact some droplets merge with others to form larger droplets which share a merged skin. In this transition case there are still discrete droplets, albeit fewer than were delivered, but individual droplets are still detectable in the sealant structure and their cumulative encapsulating skins form a surface skin for the sealant structure. At 0.7 ml/minute of combined liquids, concentrations below 10 mg/ml produced uniform polymer sealant structures lacking any discrete droplet structure and lacking the novel encapsulating skins which cumulatively provide the sealant structure surface skin.

As mentioned above, it is preferred to employ a fibrin monomer composition to prepare the present sealant structures since the monomer already has had at least one of fibrinopeptides A and/or B cleaved from the fibrinogen and is "primed" for rapid commencement of polymerization. Also mentioned above is U.S. Pat. No. 5,750,657 which describes useful fibrin monomer methods and compositions. It is preferred that such fibrin monomer compositions are autologous, i.e., prepared from the blood of the ultimate recipient. In processes from the preparation of fibrin monomer compositions a carryover of several other plasma proteins can occur. This co-harvestation of plasma proteins is alluded to in the '657 patent and described in detailed embodiments in U.S. Ser. No. 09/094,239, now U.S. Pat. No. 6,768,483. Using fibrin monomer compositions having these coharvested proteins, especially in an autologous form, is preferred when preparing the sealant structures of the present invention. Accordingly, preferred sealant structures herein will also contain these coharvested proteins within the sealant structure. Fibrin monomer compositions from which the present sealant structures can be prepared may therefore include, in addition to fibrin monomer, prothrombin, factor XIII, plasminogen, fibronectin, antithrombin III and factor X. The amount of these carryover proteins will depend upon the individual blood donor and the process used. For example, starting compositions prepared in accordance with U.S. Ser. No. 09/094,239, now U.S. Pat. No. 6,768,483 which are in turn useful to prepare the present sealant structures may include:

10–30 mg/ml of fibrin monomer;

10–40 $\mu$g/ml of prothrombin;

>9 $\mu$g/ml of factor XIII;

100–200 $\mu$g/ml of plasminogen;

60–210 $\mu$g/ml of fibronectin;

>50 $\mu$g/ml of antithrombin III; and

2–7 $\mu$g/ml of factor X.

These components and ranges are meant to be exemplary rather than limiting. The important point is that autologous solutions of fibrin (monomer) which include co-harvested proteins likely further enhance the properties of the present sealant structures in that they are a very "natural" composition to the recipient, albeit having a modified and enhanced physical structure via the encapsulated droplet geometry.

As mentioned above, it is understood that fibrin sealants resulting from components of varying fibrinogen, thrombin or fibrin monomer concentrations will have varying clot structures of the polymerizing fibrin gel itself. For example, in WO 96/22115 and WO 98/02098 the relationship of pore size and regularity is linked to the polymerization rate of the fibrin polymer as influenced by concentration of fibrinogen and/or thrombin. At higher concentrations, more rapid polymerization is obtained and WO 96/22115 and WO 98/02098 state that this results in smaller pore sizes. These patents also indicate that the polymer structure as related to the pore size has a direct influence upon the efficacy of the resulting fibrin sealant for particular applications. Some of the films described in WO 96/22115 and WO 98/02098 having smaller pore size are described as being suitable for prevention of post surgical adhesions, but are not necessarily hemostatic or adhesive. Other films generated at lower concentrations having larger pore sizes are more adhesive and hemostatic, but do not prevent post surgical adhesions. It appears that in a surgical setting where bleeding and post surgical adhesions are both expected to be a problem, a two- or three-part fibrin structure must be utilized in accordance with WO 96/22115 and WO 98/02098, with one of the parts needing to be pre-formed ex vivo. Further, the effects, if any, of pore size/sealant structure upon cell migration as may be predictive of angiogenesis and tissue repair are not disclosed.

The sealant structure in accordance with the present invention provides at least comparable, and typically superior, results in the areas of hemostasis, prevention of post surgical adhesions and tissue repair in a safe and more convenient manner. It has now been discovered that a single sealant structure of the present invention can simultaneously provide hemostasis, adhesion, prevention of post surgical adhesions and significantly enhanced cell migration across the sealant surface. Not only are multiple layers not required as compared to the prior art, but these beneficial results common to the present sealant structures over a wide range of concentrations resulting in a wide range of pore sizes and fibrin structures within the fibrin polymer. This is because a common element of all the sealant structures of the present invention is the formation of a novel high concentration fibrin skin during delivery. Preferably this is a skin encapsulating droplets during spray delivery such that the droplets not only begin to polymerize, but the concentrated fibrin polymer encapsulating skin forms around each droplet so that they maintain their discrete geometry while building the sealant structure. This unique encapsulating skin has not been disclosed in prior art sealants. The resulting surface skin of the present sealants, which is the cumulative result of many of the encapsulating skin being aligned side-by-side to form the surface skin, is also unique and novel. Thus, important aspects of the present invention are the use of the present sealant structure to provide more simple, cost-effective methods of use which also provide unexpectedly superior results in the areas of hemostasis, adhesion, sealing of fluid leaks, e.g., liquids like blood, CSF, and air, angiogenesis and tissue repair, prevention of seroma formation, prevention of post surgical adhesions, spray delivery of cells.

Indeed, in the area of post surgical adhesion prevention, prior art fibrin sealant layers need to have certain thickness ranges. As to thickness, the plurality of encapsulating skins which make up the surface skin appear to provide the cell-to-cell interaction (hemostasis, cell migration), or lack thereof, (prevention of post surgical adhesion) needed to provide the beneficial effect. A thinner sealant structure of the present invention provides substantially the same effect as a thicker layer at a given point in time. It is understood, of course, that, depending upon the rate of fibrin degradation of the sealant structure, the sealant structure may be applied to a certain thickness to provide a desired residence time, but the structure need not otherwise be of a minimum thickness for its cell interaction/cell barrier qualities to be realized.

Also, according to the prior art, sealants for sealing higher pressure fluid leaks, e.g., air leaks, are disclosed as requiring reinforcing polymer (other than fibrin) additives for greater elasticity, tensile strength and structural integrity. In this case, additives can typically be avoided because the elasticity, tensile strength and structural integrity of the present sealant structure, in addition to be dependent on thickness and fibrin concentration, are substantially enhanced by the action of the plurality of adhesive, plate-like droplets sliding, and yet adhering, in response to physical stress. That is, this physical characteristics of the present sealant structure provide an added level of flexibility and adhesiveness suitable for higher pressure fluid leaks.

Both of those properties, i.e., film barrier and enhanced flexibility provide that the sealants of the present invention also yield superior results in prevention of seroma formation.

Further, it has been found that the sealant process of the present invention is extremely useful in cell delivery. Cells suitable for delivery with the present sealant include keratinocytes and embryos.

The present fibrin polymer structure has been referred to as a fibrin sealant or sealant structure throughout this application and it has been described as providing enhanced methods for a number of uses. It should be understood that the present structures can be useful in any known fibrin sealant use and that any other use of fibrin polymer, regardless of whether or not being used as a sealant, could benefit from the novel structure and characteristics described herein.

EXAMPLE 1

A fibrin sealant in accordance with the present methods was prepared as described by Edwardson et al. in U.S. Pat. No. 5,750,657 and using a process and apparatus as disclosed by Holm, inter alia, in U.S. Pat. No. 5,741,428, U.S. Pat. No. 5,603,845, U.S. Pat. No. 5,824,230 and U.S. Pat. No. 5,958,253.

Freshly drawn anti coagulated whole blood (120 ml plus 17 ml 4% trisodium citrate USP) was centrifugally separated and the resulting plasma (60 ml) reacted with biotin-batroxobin for 10 minute at 37° C. The acid soluble fibrin I polymer produced was isolated by centrifugation and dissolved in 3.5–5.2 ml 0.2M sodium acetate buffer (pH 4) containing calcium ions.

Approximately 6 ml of concentrated fibrin I (20±2 mg/ml) which is stable for several days at −20° C. resulted. Trace amounts of biotin-batroxobin were removed by addition of freeze-dried avidin covalently coupled to agarose, which hydrates the fibrin I. Within 5 minutes the biotin-batroxobin:avidin-agarose was removed by filtration and the concentrated fibrin I monomer was transferred to the desired applicator devices for use in the following experiments.

The resulting F1 monomer solution was co-applied with a carbonate/bicarbonate buffer (pH 10) in a ratio of 7:1 (F1:pH 10).

EXAMPLE 2

This study was constructed to assess the effect of the fibrin monomer sealant of Example 1 (hereinafter "F1 monomer sealant") on post-surgical flexor tendon adhesion formation in a rabbit experimental model. Further subdivision into mobilized and immobilized postoperative groups allowed assessment of any synergy between the F1 monomer sealant and a method well documented to reduce adhesion formation, namely early active mobilization.

Materials and Methods
Animal Model and Surgical Procedure

20 Murex Lop rabbits were used for this study. They were of equal sex distribution and the body weight ranged from 2500 to 4500 grams. There was one death prior to end point assessment making the total number of rabbits 19 (9 male, 10 female). The animals were obtained at least seven days prior to surgery from Murex BioTech Ltd (Dartfort, Kent) to allow for acclimatization. Throughout the study period they were housed in single cages and fed and watered ad libitum. Regular assessment of the animals' general condition and surgical wound were carried out in accordance with the U.K. Home Office "Guide for the Care and the Use of Laboratory Animals" 1996.

The surgical procedure was carried out in a fully equipped operating theatre, which was "Good Laboratory Practice" compliant. Induction of anaesthesia was by Hypnorm® (Janseen Copenhagen, Denmark, 0.2 ml/kg, im) followed by Diazeparm (Phoenix, 0.5 ml/kg, iv). Maintenance was via an anaesthetic mask, which delivered 2% halothane (Zeneca) and oxygen flowing at 2l/min. The condition of the anaesthetised animals was continuously monitored using a pulse and oxygen saturation probe. Recovery from anaesthesia was encouraged with pure oxygen delivery via the facemask.

Prior to the start of the procedure the left front paw's flexor aspect was shaved with hair clippers. After anaesthetic induction the operative site was prepared with chlorhexidine in alcohol and iodine in alcohol scrubs. The field was isolated with sterile drapes. With the aid of an operating microscope, the second and fourth digits of the left front paw were longitudinally incised over the base of the proximal phalanx. Blunt dissection in the midline revealed the digital sheath and its tendinous contents. The sheath was then opened between pulleys A2 and A3 (a point corresponding to the middle of the proximal phalanx). Flexor digitorum profundus was exposed (FIG. 1). This long flexor tendon of digits two and four then received a standard surgical injury on its volar aspect with a 15 blade. The injury measured 5 mm in length and exposed the core substance of the tendon. Prior to wound closure the flexor digitorum profundus wounds of digit two and four were either treated with F1 monomer sealant (FIG. 3) or received no treatment. Application of F1 monomer sealant (between 0.1–0.4 mls) was through a variable fine jet applicator as disclosed in WO 97/20585 and WO 98/20931. The resultant coating was allowed to polymerise in air for 3 minutes and the injured tendon was then returned to the base of the wound. The operated untreated digits also received 3 minutes of air exposure. All second digits were immobilised with the additional surgical procedure of proximal tendon transaction. This was performed through a transverse skin incision just distal to the carpal tunnel. Both flexor digitorum profundus and flexor digitorum superficialis to digit two were sharply transacted in the palm thus immobilising the digit. All skin incisions were closed with subcuticular interrupted horizontal mattress sutures (4/0 Vicryl (Ethicon)). The wound was then dressed with Cicatrin® (Wellcome) antimicrobial powder and sprayed with Opsite® (Smith and nephew). No external dressings were applied. All animals received buprenorphine (0.01–0.05 mg/kg) for postoperative analgesia. After recovery animals were allowed to move about as normal in their cages. At 14 days post surgery, the animals were euthanased using a lethal barbiturate intravascular injection.

Biomechanical Assessment of Adhesion Development

Adhesion development was assessed by the use of a tensiometer in all operated groups. In addition the animals unoperated right front paw (digits two and four) were assessed in the same way so as to provide an unoperated control group for comparative analysis. Double blind biomechanical assessment was therefore conducted on 5 groups.

Group 1 Unoperated controls.
Group 2 Immobilised (digit 2) operated and F1 monomer sealant tested.
Group 3 Mobilised (digit 4) operated and F1 monomer sealant tested.
Group 4 Immobilised (digit 2) operated and no further treatment.
Group 5 Mobilised (digit 4) operated and no further treatment.

The tensiometer (NE Holm A/S, Denmark) measured the force in grams required to pull the flexor digitorurn profundus tendon from its sheath. The freshly culled animals' front left and right second and fourth digit were each dissected and the flexor digitorum superficialis and flexor digitorum profundus were transacted proximal and distal to the operative injury site. The proximal dissection culminated in transacting the two tendons approximately 15 mm proximal to the mouth of the digital sheath. The distal dissection culminated in the flexor digitorum profundus tendon being transacted between the A3 and A4 pulley making sure that this was proximal to the insertion of the vincular vessels. The proximal stump of the flexor digitorurn profundus tendon was then transfixed with a silk 2/0-stay suture. With the nail of the relevant digit held rigid in a clamp, the silk tie was then connected to the tensiometer. The force required to pull the tendon free from the sheath was recorded in grams and was indicative of adhesion build-up.

Statistical assessment of the observed data was carried out using a robust regression technique in a Stata Release 6 statistical software package. This analysis accounted for the structure of the data, which consisted of several measurements per animal. This technique specifies that there is inter but not necessarily intra animal observation independence. Robust estimates of the standard errors of regression coefficients were calculated using the Huber/White/sandwich estimator. This takes into account the potential lack of independence from the same sample. The residual variances were not constant between groups on the original scale of measurement. They were therefore not normally distributed. The statistical analysis was therefore performed after applying a $\log_{10}$ transformation. Regression analysis obtained estimates of geometric mean tension and 95% confidence intervals per group. To obtain these values the coefficients and confidence intervals on the logarithmic scale were transformed back into the original scale of measurement (Table 1 and 2). The raw data has been graphed on a box and whisker plot (Sigma Plot version 4.0). The boxes correspond to the interquartile range (the central 50% of the data) with an internal line to mark the median. The mean is represented with a dotted line. The length of the whiskers are 1.5 times the interquartile range. Values outside the whiskers have been plotted individually.

Results

This study used 20 rabbits. One died prior to biomechanical assessment. They were randomly assigned to one of four treatment groups or an unoperated control group. The potential maximum number of observations of the 19 rabbits was 76, four per rabbit. However out of these only 67 were suitable for statistical analysis (88%) due for example to the tendon snapping in the mobile group, or incomplete distal transaction prior to tensiometer pull. Statistical assessment was therefore performed on the following number of tendons per group. Group 1 (n=36) Group 2 (n=7) Group 3 (n=6) Group 4 (n=10) and finally Group 5 (n =8).

The raw tensiometer pulls mean value for each group is graphically represented in graph 1. Interpretation of the raw data revealed an overall reduction in pull required to remove the tendon from its sheath by 75.6% when comparing the total treated F1 monomer sealant groups. When separated into mobile and immobile the reduction from untreated to treated groups was 79.7% and 76.8% respectively.

As previously stated the group data was not normally distributed. Meaningful interpretation of the raw data required application of a logarithmic scale. Table 1 shows the geometric mean tension values and 95% confidence intervals for the mean per group. Comparison was made between operated groups and unoperated controls using robust regression analysis. This analysis demonstrated no statistical difference when comparing the F1 monomer sealant treated groups (immobilised p=0.42, and mobilised p=0.47) with the normal unoperated control pulls. This implies there was no significant difference in adhesion formation between F1 monomer sealant treated injuries and unoperated controls. There was however a highly significant difference with comparisons made between the operated untreated groups and the unoperated controls (immobilised p<0.001, and mobilised p<0.001). This indicated that without treatment with F1 monomer sealant, surgical injury produced significant increases in adhesion formation, as evaluated by tensiometer pull in comparison to the unoperated controls. Further analysis of the data shows that between the operated groups with the same type of post operative mobilisation, the addition of F1 monomer sealant makes a significant difference (difference between F1 monomer sealant immobilised and untreated immobilised p=0.03, difference between F1 monomer sealant mobilised and untreated immobilised p=0.03). After performing regression analysis on the $\log_{10}$ of the raw data, percentage change in mean tension from unoperated control side was as follows:

Group 2 Immobilised operated and F1 monomer sealant treated (increased by 72%)
Group 3 Mobilised operated F1 monomer sealant treated (increased by 39%)
Group 4 Immobilised operated and no further treatment (increased by 980%)
Group 5 Mobilised operated and no further treatment (increased by 490%)

Figure 7:
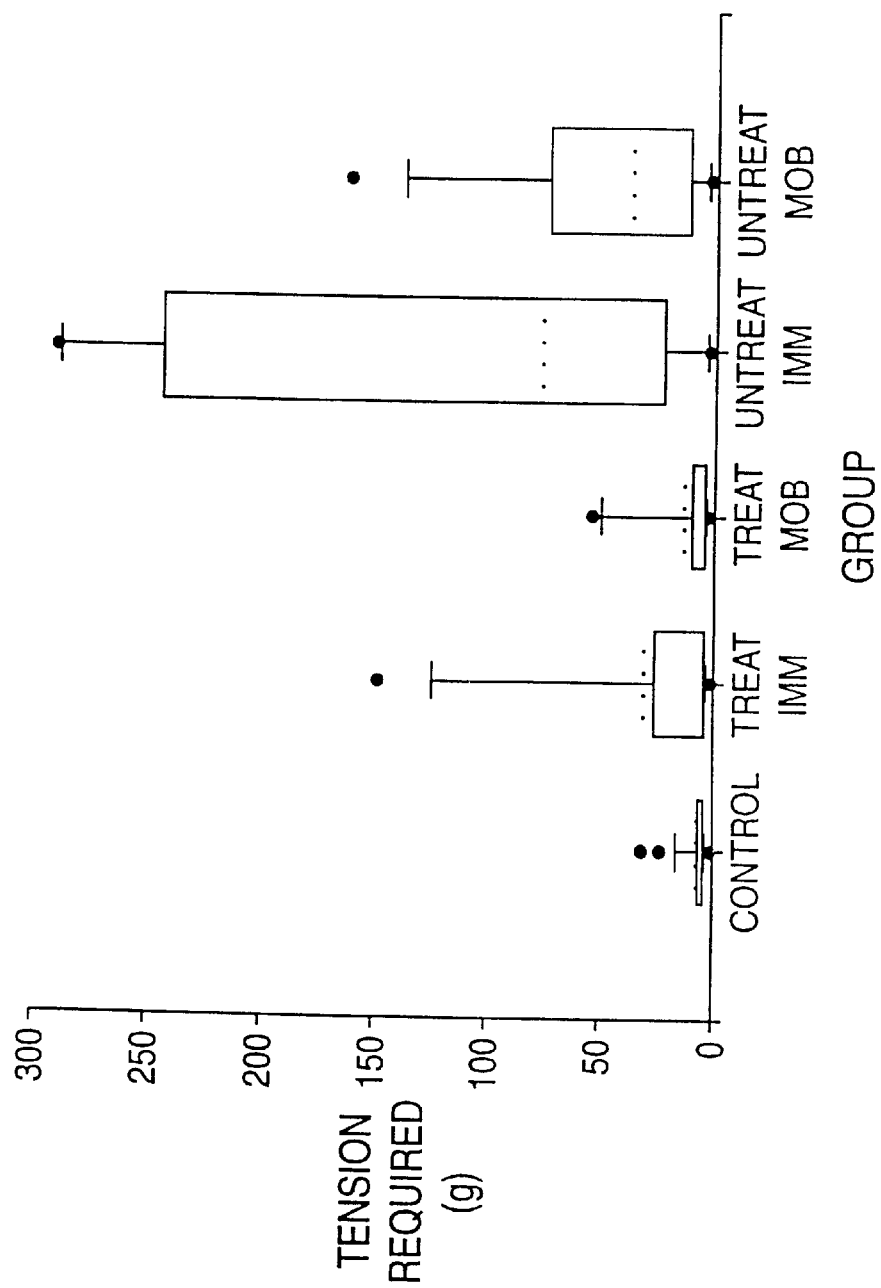
FIG. 7 Is a Box and Whisker raw data plot of raw tensionmeter pulls mean values.

From these data it can be concluded that both the mobile and immobile F1 monomer sealant treated groups were not significantly different to unoperated control group (P=0.47 and P=0.42 respectively Table 2). The raw data graph provided in FIG. 7 shows that F1 monomer sealant works in combination with active mobilisation to reduce the forces required to pull the tendon from the sheath, indicating a considerable reduction in adhesion generation in treated eases. This is contrasted with the comparison made between the unoperated control group and the operated untreated group. Both the mobile and immobile untreated groups form significantly more adhesion than the unoperated control (P=0.001 respectively (Table 2)). Again the raw data graph provided in FIG. 7 does show the benefits of mobilisation in the reduction of adhesion formation.

Box and Whisker plot of raw data. The boxes correspond to the interquartile range (the central 50% of the data). The solid internal line represents the median value. The dotted horizontal line is the mean value. The length of the whiskers are plotted individually. Points outside these are individually graphed.

TABLE 1

The geometric mean tension and 95% confidence intervals for the mean per group

| Group | Geometric Mean Tension | 95% confidence interval for the mean |
|---|---|---|
| Unoperated control | 1.5 | 0.4 to 2.9 |
| Vivostat Immobilised | 4.7 | −1. to 26.3 |
| Vivostat Mobilised | 3.2 | −0.5 to 12.6 |
| No Treatment Immobilised | 45.1 | 13.0 to 142.0 |
| No Treatment Mobilised | 23.4 | 7.1 to 66.3 |

TABLE 2

P Values from the robust regression analysis comparing every pair of group means.

| | Unoperated control | Vivostat Immobilised | Vivostat Mobilised | No Treatment Immobilised |
|---|---|---|---|---|
| Vivostat Immobilised | 0.42 | | | |
| Vivostat Mobilised | 0.47 | 0.77 | | |
| No Treatment Immobilised | <0.001 | 0.03 | 0.004 | |
| No Treatment Mobilised | <0.001 | 0.13 | 0.03 | 0.42 |

EXAMPLE 3

The clinical performance of fibrin sealants is influenced by physical properties such as elasticity, tensile strength, and ability to adhere to human tissue. These properties are related to the internal structure of the fibrin sealant that builds as it polymerises. Analysis of the minimum polymerisation time to achieve a functional fibrin clot is clinically important. Instant tissue-fibrin sealant adhesion is desirable to ensure that the fibrin sealant functions on contact and remains at the site of application without being washed away by blood or displaced by movement of the target tissue (e.g., the heart or lungs). The physical characteristics of fibrin sealants are related to the extent of fibrin crosslinking. Determination of the polymerisation rate allows calculation of the minimum time required to produce a functional clot. The adhesion characteristics to vital human tissue and kinetics of polymerisation between 20 and 300 seconds post-application of Vivostat™ Fibrin 1 monomer based sealant have been analysed and compared to those obtained for two conventional fibrin sealants, Tissucol® and Beriplast®. Mathematical analysis of the experimental data revealed that polymerisation of Vivostat™ sealant followed first order kinetics whereas that of Beriplast® and Tissucol® followed second order kinetics. This study demonstrates that Vivostat™ sealant polymerises faster than conventional fibrin sealants.

1. Materials and Methods

Solutions were prepared from fresh blood donations as described in Example 1 and used within I hour. Sealant was delivered using the Spraypen™ applicator in combination with the automated Vivostat™ application unit as disclosed by Holm et al. in WO 97/20585 and WO 98/20931. Conventional fibrin sealants Tissucol® (Baxter) (1 ml and 2 ml kits) and Beriplast® (Aventis) (1 ml and 3 ml kits) were prepared and applied according to the manufacturers' instructions. Tissucol® and Beriplast® were applied using the Duploject® and Pantaject® applicators, respectively, fitted with a needle or a spray head.

Torsion rheometry experiments were performed using a controlled stress rheometer, Carri-Med CSL 100 auto gap. Approximately 0.5 ml of fibrin sealant was applied on to the bottom of the rheometer. The top was a 2 cm diameter fine-hatched plate and the sample platform consisted of a 2 cm diameter fine-hatched plate over a Peltier baseplate. The temperature of the rheometer was set at 37° C. Oscillation experiments were performed using a constant oscillation torque of 15 μNm at a frequency of 0.1 Hz for 11 minutes.

Figure 3:
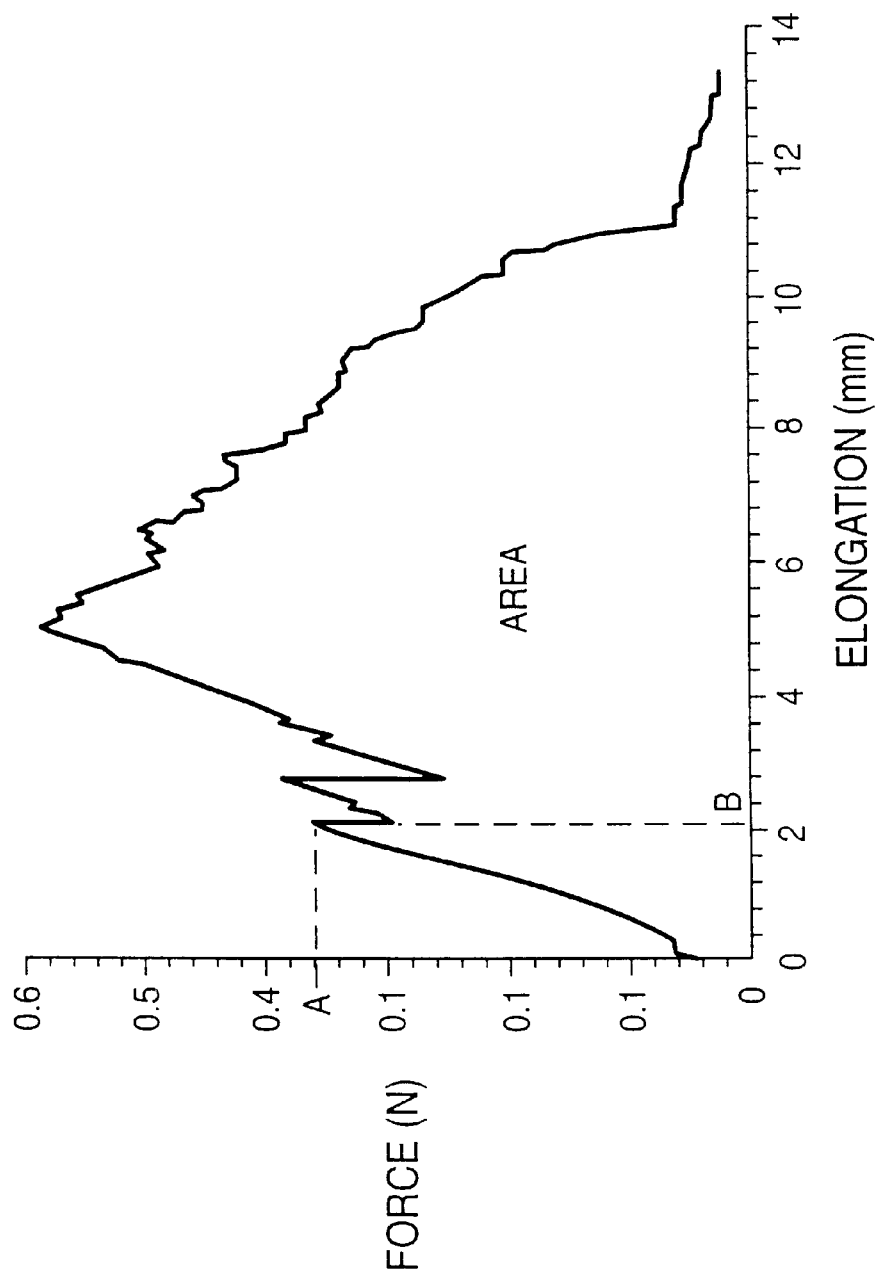
FIG. 3 Is a graph illustrating the adhesion experiment of Example 3.

Adhesion experiments were performed using a recently described model involving use of vital human tissue (Kjaergaardetal, Eur. Surg. Res. 1999). The human tissue samples were greater saphenous vein grafts left over from coronary artery bypass grafting. To ensure tissue vitality, all samples were kept in physiological saline solution and used within 24 hours of harvesting. The vein graft was split longitudinally and the split graft was cut into 1 cm² samples that were fixed to the sample holder using Gore-Tex VS retaining sutures. The two samples were brought into close proximity at an angle of 450, and 0.1 ml of fibrin sealant was sprayed on the tissue surfaces, where the adventitia was exposed. The two tissue samples were brought into contact without external pressure and were left polymerised until the adhesion experiment began. Tests were performed using a Nene universal testing machine model MS at a speed of 10 mm per minute. Adhesion strength defined as force divided by the cross-sectional area of the sample, adhesion energy (i.e., area under the experimental curve as seen in FIG. 3), and elongation (i.e., extension reached by the specimen) were calculated for each experiment. Mean values were calculated at each polymerisation time. Confidence intervals (i.e., 95% CI) were also calculated for each parameter as 95% CI=1.95·CV/√n, where n is the number of samples analysed and CV=6.60, 8.35, and 9.81% for the adhesion strength, extension and adhesion energy, respectively.

2. Results

Sixteen solutions, each prepared from fresh blood donations from different donors, were sprayed on to the rheometer stage, and the rheology of the fibrin clot formed was studied over a period of 11 minutes. The average fibrin I concentration was 22.20 mg/ml±12.7%(CV). Four samples of Tissucol® and Beriplast® were also analysed the rheometer.

Curve fitting analysis of dG'/dt against time revealed that the polymerisation of sealant followed first order kinetics as shown in equation (1) where t is the time, $(dG'/dt)_o$ is the value of the derivative at t=0 and k is the kinetic rate constant:

$$\frac{dG'}{dt} = \frac{(dG')}{(dt)_0} e^{-kt} \quad (1)$$

A single curve showing dG'/dt versus time was prepared averaging the values for the sixteen samples at each time point. The values obtained for k and $(dG'/dt)_0$ were $1.17 \cdot 10^{-2} \pm 0.05 \cdot 10^{-2}$ s$^{-1}$ and 3.17±0.15 pa s$^{-1}$, respectively (r=0.9926; X²=0.0683).

Analogous mathematical analysis was applied to samples of Tissucol® and Beriplast® fibrin sealants. An attempt to fit the experimental data to equation (1) gave a very poor correlation (r=0.8300–0.9400). In this case, dG'/dt followed second order kinetics as shown in equation (2) where t is the time, $(dG'/dt)_o$ is the value of the derivative at t=0 and k is the kinetic rate constant in pascals$^{-1}$.

$$\frac{(dG')}{(dt)} = \frac{1}{kt \frac{1}{(dG')} (dt)_o} \quad (2)$$

Kinetic parameters for Tissucol® and Beriplast® were calculated by fitting the average dG'/dt curve to equation (2). Table 3 shows the results obtained following this procedure. For conventional fibrin sealants, the mixing efficiency of the two components of the fibrin sealant had a great influence on the speed of formation of the clot. Spray delivery systems increased the kinetic rate constant by almost 43% for Tissucol® and by 18% for Tissucol®.

Figure 4:
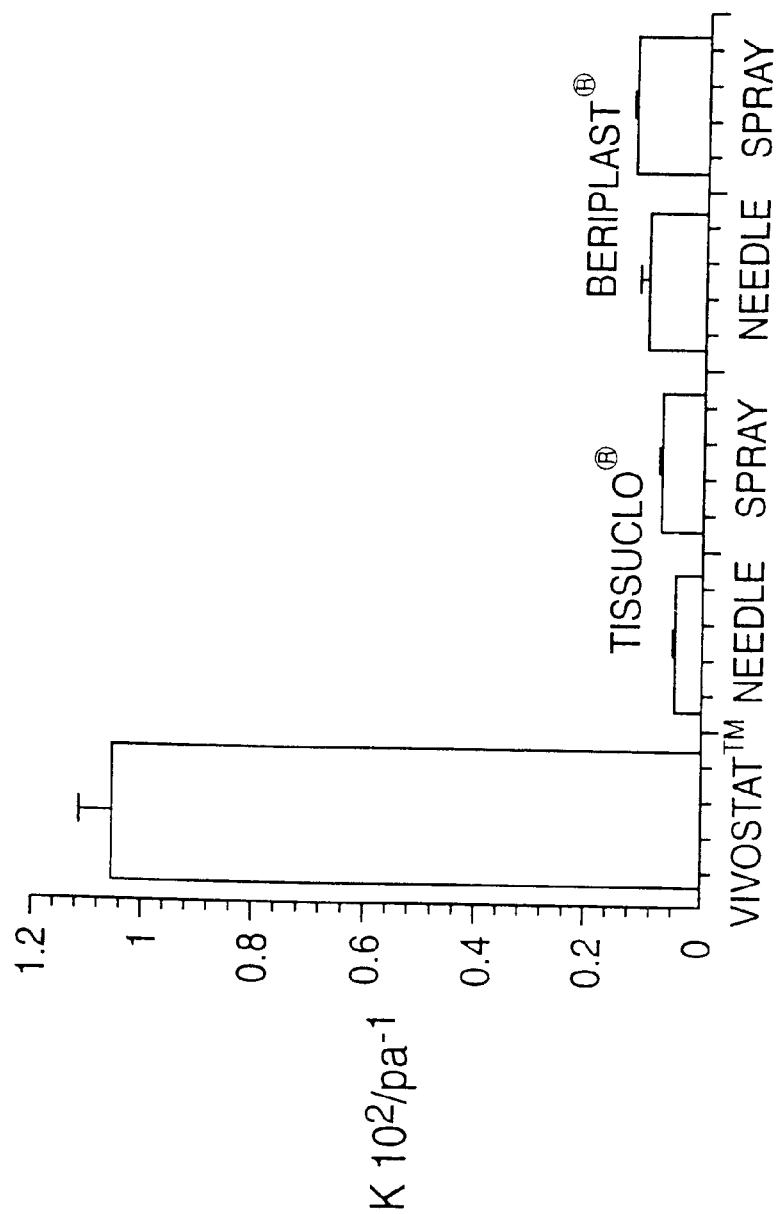
FIG. 4 Is a graph comparison of Vivostat™, Tissucol® and Beriplast® kinetic rate constants based on a second order reaction over the initial 200 seconds of polymerisation.

The kinetics of polymerisation of Tissucol® and Beriplast® were compared over the first 200 seconds of polymerisation. Over this period of time and for the sake of comparison, the experimental curve can be fitted using the second order kinetics model represented by equation (2) with a good correlation (r=0.9974). In this case, the kinetic rate constant exhibited a similar absolute value (i.e., k=1.06·10$^{-2}$±0.06·10$^{-2}$ pa$^{-1}$) to that obtained using equation (1). Results are summarised in FIG. 4. As shown, the second order kinetic rate constant was between 6 and 20 times greater than the other fibrin sealants.

Adhesion experiments were performed on samples of sprayed fibrin sealant in order to compare similar application systems. Most of the samples showed a first breaking point (i.e., intersection of points A and B, see FIG. 3) before the maximum force was reached. This point was detected by a sudden reduction in adhesion force (FIG. 3) and was visually observed as a partial breaking of the sample. This represents the limit of the elastic character of the sealant and the first failure of the system, which has clear implications from a clinical point of view. Elongation at first breaking point (i.e., elongation at B) and adhesion strength at first breaking point (i.e., force at point A divided by the cross-sectional area) were measured for each sample. Maximum adhesion strength and elongation as well as adhesion energy (i.e., area under the experimental curve) were also calculated. Two identical adhesion experiments were prepared at each time point and the mean value recorded for each sealant sample. Results are summarised in Tables 4–6.

Figure 5:
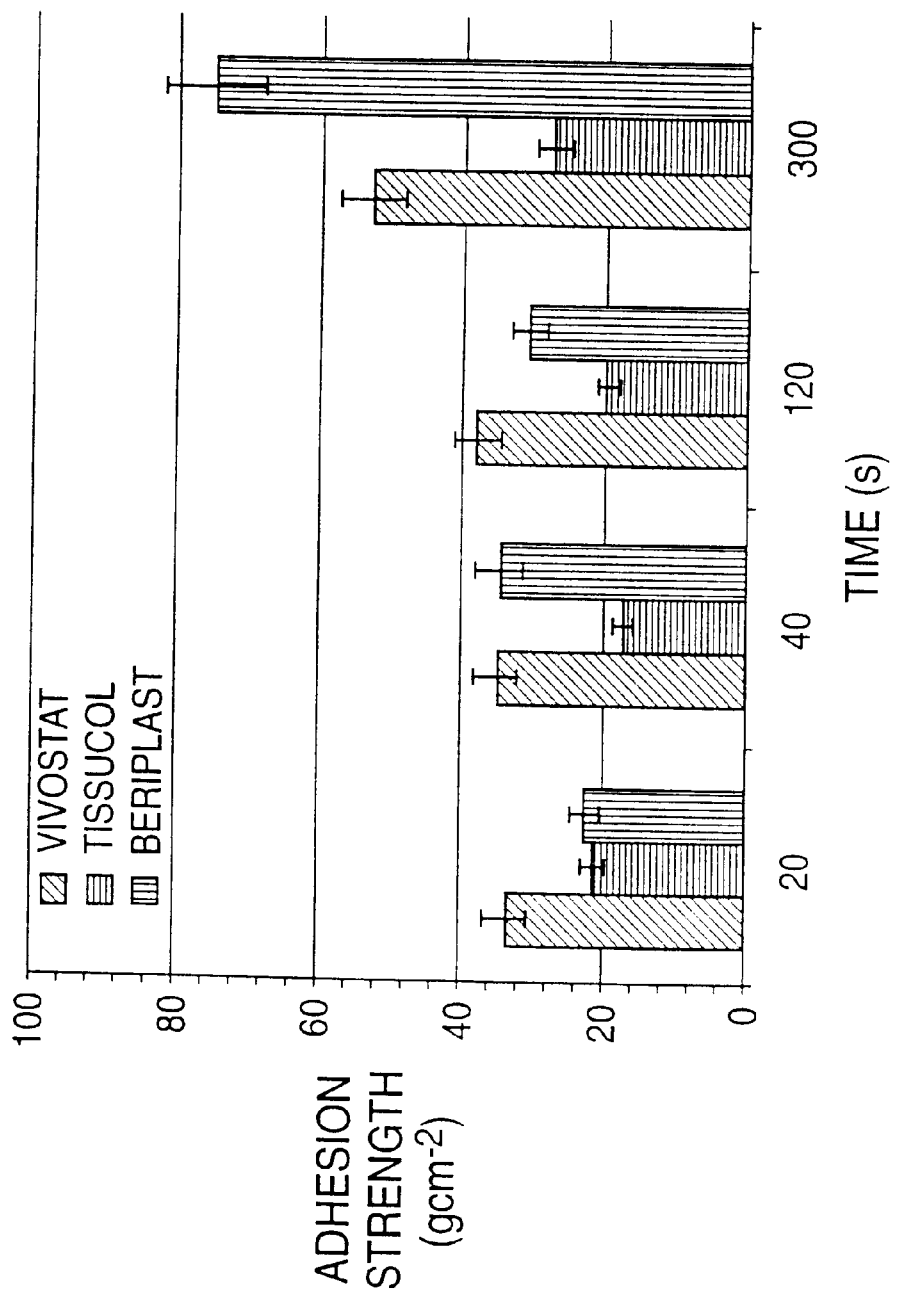
FIG. 5 Is a graph illustrating adhesion strength at first breaking point at various polymerisation times for of Vivostat™, Tissucol® and Beriplast®.
Figure 6:
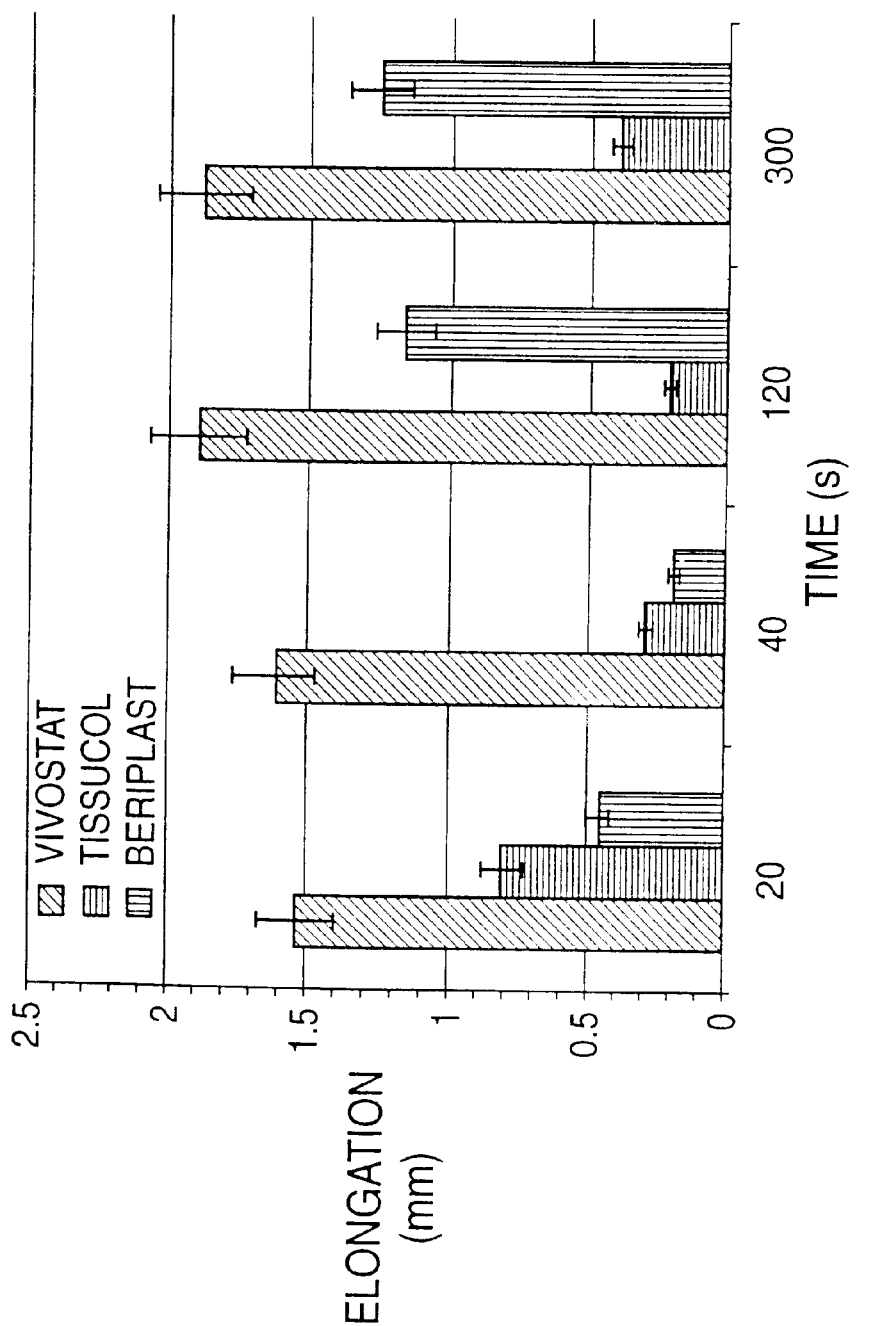
FIG. 6 Is a graph illustrating elongation at first breaking point at various polymerisation times for Vivostat™, Tissucol® and Beriplast®.

Reached a high degree of elasticity much faster than either Tissucol® or Beriplast®. This is consistent with the kinetic analysis showing that the polymerisation rate was much faster than that of competitor products. As a result, superior instant adhesion to tissue (FIG. 5) as well as better elastic characteristics (FIG. 6).

TABLE 3

Kinetic parameters and regression analysis correlation for Tissucol ® or Beriplas ® fibrin sealants

| Applicator | $(dG'/dt)_0$/pa s$^{-1}$ | k 10$^3$/pa$^{-1}$ | r | x² |
|---|---|---|---|---|
| Tissucol ® | | | | |
| Needle 3.20 | 14.15 ± 0.43 | 0.48 ± 0.02 | 0.9893 | |
| Spray 5.53 | 54.19 ± 4.71 | 0.84 ± 0.04 | 0.9934 | |
| Beriplast ® | | | | |
| Needle 8.80 | 19.75 ± 1.65 | 1.11 ± 0.07 | 0.9739 | |
| Spray | 29.22 ± 4.35 | 0.84 ± 0.04 | 0.9615 | 6.56 |

TABLE 4

Adhesion properties ±95% CI for Vivostat ™ fibrin sealant

| | Time (seconds) | | | |
|---|---|---|---|---|
| | 20 | 40 | 120 | 300 |
| Adhesion strength (gcm$^{-2}$) | 36.35 ± 3.31 | 34.83 ± 3.17 | 37.80 ± 3.44 | 53.13 ± 4.84 |
| Elongation (mm) | 18.36 ± 2.11 | 15.73 ± 1.81 | 14.20 ± 1.63 | 11.56 ± 1.33 |
| Elongation at first break (mm) | 1.54 ± 0.18 | 1.62 ± 0.19 | 1.90 ± 0.22 | 1.88 ± 0.22 |
| Adhesion strength at first break (gcm$^{-2}$) | 33.65 ± 3.06 | 34.83 ± 3.17 | 34.67 ± 3.16 | 34.67 ± 3.16 |
| Adhesion energy (mJ) | 3.12 ± 0.42 | 2.81 ± 0.38 | 2.47 ± 0.33 | 2.99 ± 0.40 |

TABLE 5

Adhesion properties ±95% CI for Tissucol ® fibrin sealant

| | Time (seconds) | | | |
|---|---|---|---|---|
| | 20 | 40* | 120 | 300 |
| Adhesion strength (gcm$^{-2}$) | 24.94 ± 2.68 | 40.92 ± 5.26 | 65.39 ± 5.95 | 81.11 ± 7.38 |
| Elongation (mm) | 4.45 ± 0.51 | 6.38 ± 1.04 | 8.14 ± 0.94 | 11.65 ± 1.34 |
| Elongation at first break (mm) | 0.80 ± 0.09 | 0.29 ± 0.05 | 0.21 ± 0.02 | 0.39 ± 0.04 |
| Adhesion strength at first break (gcm$^{-2}$) | 21.41 ± 1.95 | 17.34 ± 3.32 | 19.37 ± 1.76 | 27.53 ± 2.51 |
| Adhesion energy (mJ) | 0.68 ± 0.09 | 1.65 ± 0.32 | 2.41 ± 0.33 | 6.29 ± 0.85 |

*Single experiment

TABLE 6

Adhesion properties ±95% CI for Beriplast ® fibrin sealant

| | Time (seconds) | | | |
|---|---|---|---|---|
| | 20 | 40 | 120 | 300 |
| Adhesion strength (gcm$^{-2}$) | 49.95 ± 4.55 | 93.61 ± 8.52 | 131.64 ± 11.98 | 168.35 ± 15.32 |
| Elongation (mm) | 6.60$^{-2}$0.76 | 4.23 ± 0.49 | 11.84 ± 1.36 | 18.48 ± 2.13 |
| Elongation at first break (mm) | 0.46 ± 0.05 | 0.19 ± 0.02 | 1.17 ± 0.13 | 1.25 ± 0.14 |
| Adhesion strength at first break (cm$^{-2}$) | 22.43 ± 2.04 | 34.67 ± 3.16 | 30.59 ± 2.78 | 75.46 ± 6.87 |
| Adhesion energy (mJ) | 1.41 ± 0.19 | 1.58 ± 0.21 | 7.53 ± 1.02 | 7.59 ± 1.03 |

EXAMPLE 4

The purpose of this Example 4 is to evaluate the ability of three fibrin sealants in the prevention of post surgical adhesion (PSA) in the peritoneal cavity of rabbits following surgical injury to the uterine horn and the opposing ipsilateral peritoneal wall. This example evaluate syringe-applied sealants as follows:

a) the Vivostat™ fibrin I monomer-based fibrin sealant as used in the earlier examples;
b) Tissucol®, a fibrin sealant which was commercially available in Europe through Immuno AG in Austria, and which is a two component sealant system involving the coapplication of pooled human fibrinogen (in an aprotinim-containing solution) and a bovine thrombin component in a calcium chloride solution; and
c) Cyroprecipitate (CYRO), a cryoprecipitate concentrated blood component containing fibrinogen from a single donor and co-applied with bovine thrombin.

The Tissucol® and CRYO were all evaluated with 4 units and 500 units of bovine thrombin.

Model

In summary a standard abrasion injury was inflicted on each uterine horn and ipsilateral peritoneal] wall, which would naturally lie in juxtaposition.

The injured areas were then held apposed using positional sutures, placed outside the experimental site, with treated sites separated by a layer of fibrin sealant. Experimental sites were then left in vivo for the length of recovery time dictated by the study protocol. Due to the level of injury induced and injured surfaces being apposed this rabbit uterine horn abrasion model is a severe experimental PSA model, with a "worse case" scenario created.

To ensure that injuries of consistent standard area could be induced, templates, 25 mm×3 mm, designed to fit the uterine horn or peritoneal wall, were specially constructed. Abrasions were induced using a scraper with a standard depth (1.5 mm) which fitted the exact area of the template. With the additional parameter of using a set number of scrapes for each injury site, injuries were maximally standardised within the limits of biological variation.

Uterine horns were chosen as the experimental site, together with the peritoneal wall, due to their size, structure and location within the peritoneal cavity. Heavy handling of tissues has been shown to induce PSA formation (Boys, 1942; Connolly & Smith, 1960) and hence excessive tissue handling needed to be avoided. In addition, ex-breeding rabbits were also chosen for these investigations due to their large size facilitating appropriate procedures.

Procedure

Premedication was administered with hypnorm (Fentanyl citrate 0.315 mg/ml and fluanisone 10 g/ml. Supplied by Janssen Saunderton, High Wycombe, Buckinghamshire.) (0.2 ml/kg body weight intramuscular) to the right gluteous maximus muscle.

Surgical anaesthesia was induced with hypnorm (0.3 ml/kg body weight intramuscular) and diazepam (5 mg/ml diazepam. Supplied by Phoenix Pharmaceuticals Limited, Gloucester.) (2.5 mg/kg body weight intravenous). Full sterile operating procedures were observed. Particular attention was paid to the washing of surgical gloves in sterile water to remove all traces of particulate matter (starch, powder) which might, if transferred to the operative site, induce granuloma or adhesion formation.

Fur was shaved from the surgical area and the area scrubbed with alcoholic chlorhexidine followed by iodine. Laparotomy was performed using cutting diathermy, by a single incision in the midline, from lower liver margin to the level of the iliac fossa, through skin and muscle to peritoneum, which was divided with scissors. Retraction was applied to laparotomy wound edges to allow access to uterine horns.

Experimental areas were selected on the serosal surface of each uterine horn and corresponding internal ipsilateral surfaces of the peritoneum, which would naturally lie in juxtaposition with each other. A standard template, constructed specifically either for the uterine horn or peritoneal wall, was placed on the selected areas and each area abraded with the sharp edge of a scraping tool. A standard number of 10 scrapes was used to cause homogeneous punctate bleeding but not so far as to cause frank contiguous hemorrhage. Hence a standard, and reproducible injury was produced in each case.

Single throws of Stannius positional suture (Ethibond 6/0 or similar) were placed 5 mm outside each end of abraded areas (peritoneal wall and uterine horn). These sutures passed only through the serosa of the peritoneum and corresponding uterine horn. For control groups, sutures were tightened to bring the two juxtapositional abraded areas together and maintain contact between the two areas. Timing was commenced from this point. For treated groups positional sutures were tightened to bring the two abraded areas close together but not in contact and fibrin sealant was then applied to abraded areas. Sutures were then drawn together to bring the two areas into contact, using as much tension as was needed to create reasonable contact but avoiding tight sutures. Timing commenced from this point.

In groups which sampled up to 30 minutes post injury, rabbits were kept anaesthetised, in the supine position with the laparotomy incision held closed with tissue clamps. In groups which sampled from 1 hour post injury onwards, the laparotomy was closed and reopened after the relevant time period.

Laparotomy wound closure was in two layers: first with 2/0 plain catgut on atraumatic half round needle for the peritoneum and muscle layers, using transplant longflow, overunder, non-interrupted crossed sutures; and secondly with 2/0 Prolene or similar on half round cutting needle using interrupted mattress sutures for the skin. Immediately after closure of the wound, wound dressing was applied on and around the wound.

At 14 days post surgery animals were anesthetized (as for the surgical procedure). Laparotomy was reopened along the original incision with experimental areas identified and macroscopic observations recorded and photographed. The abraded area of the peritonem together with a border of unabraded tissue in excess of 5 mm and the associated uterine horn were resected.

A summary of the experimental groups is in Table 7 below.

| Treatment Group | Number of Animals | Number of Experimental Sites | Mean Volume of Sealant Applied (ml) | Mean Fibri I Conc$^n$ (mg/ml) |
|---|---|---|---|---|
| Control | 7 | 13 | N/A | N/A |
| Novel Fibrin Sealant (Needle Application) | 6 | 12 | 0.93 ± 0.06 | 14.90 ± 2.41 |
| Tissucol ® | 6 | Total: 11 | | 17.50–28.75 |
| 4 Units Bovine Thrombin | | 5 | 0.50 ± 0.03 | |
| 500 Units Bovine Thrombin | | 6 | 1.12 ± 0.11 | |
| CRYO | 6 | Total: 12 | | 10.64 ± 0.84 |
| 4 Units Bovine Thrombin | | 6 | 0.47 ± 0.02 | |
| 500 Units Bovine Thrombin | | 6 | 0.33 ± 0.03 | |

Results

Macroscopic Results

Figure 8:
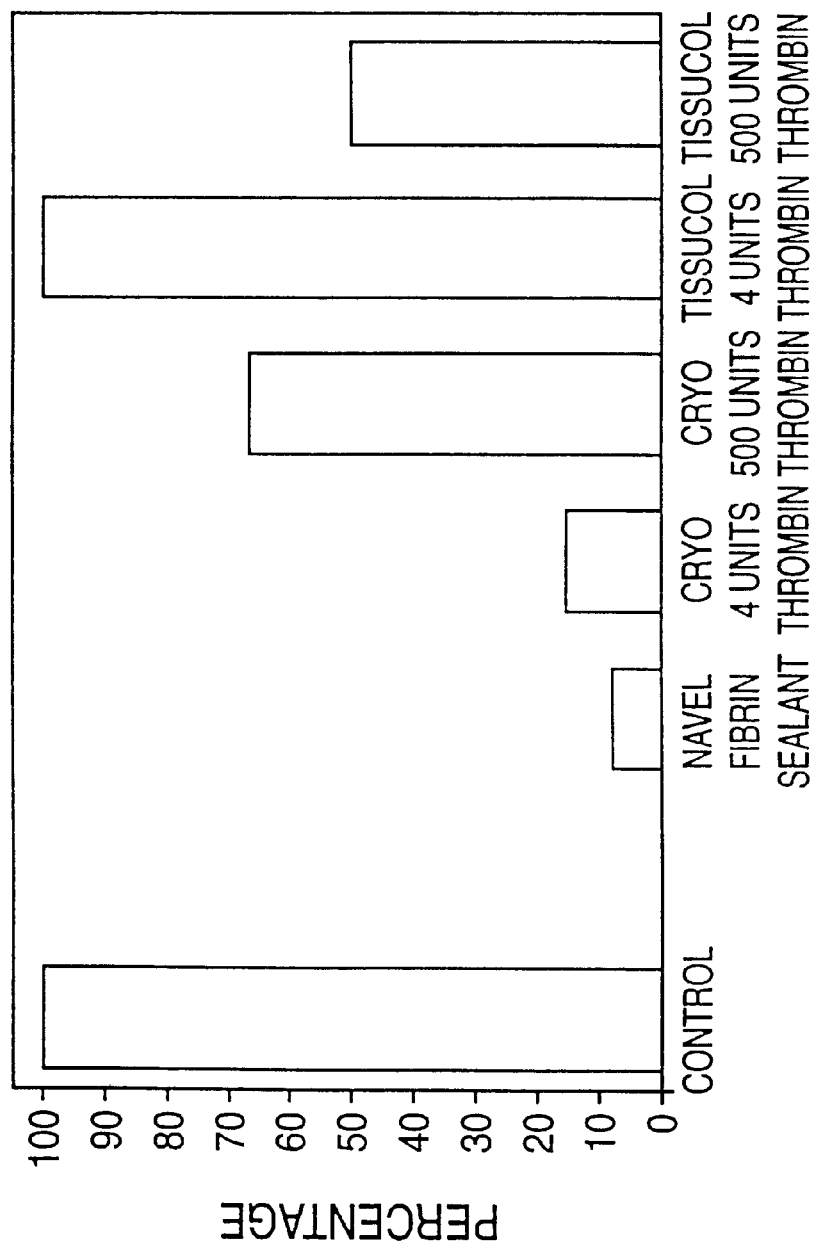
FIG. 8 Is a graphical representation of macroscopic PSA incidence.

All of the control groups (13/13) showed PSAs joining the abraded areas of the peritoneal wall and uterine horn. The macroscopic incidence of experimentally induced PSAs for treatment groups was 8.3% for Vivostat™ sealant, 16.7% CRYO 4 units thrombin, 66.7% CRYO 500 units thrombin, 100% Tissucol® 4 units thrombin and 50% Tissucol® 500 units thrombin as showin in FIG. 8.

Microscopic Quantitative Results

Figure 9:
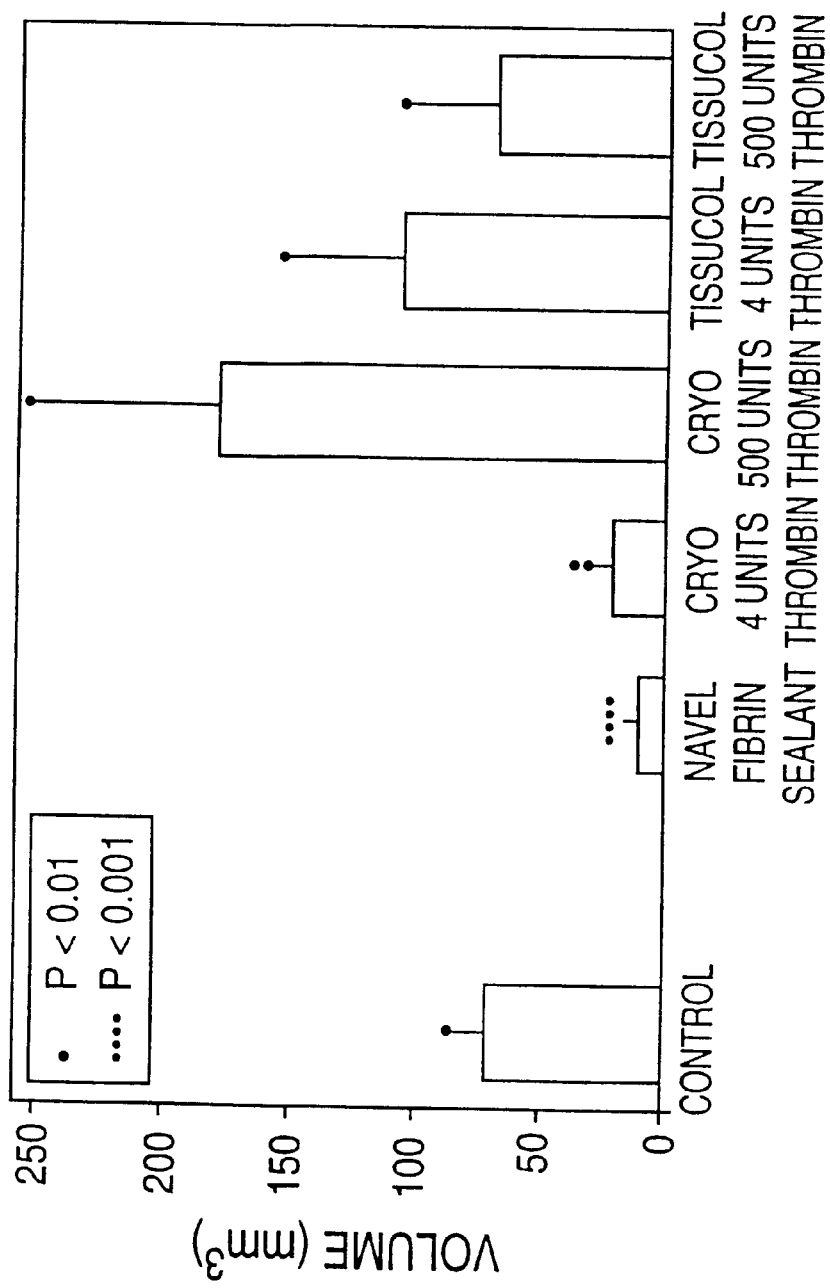
FIG. 9 Is a graphical representation of mean PSA volumes together with SEMs and statistical differences.
Figure 10:
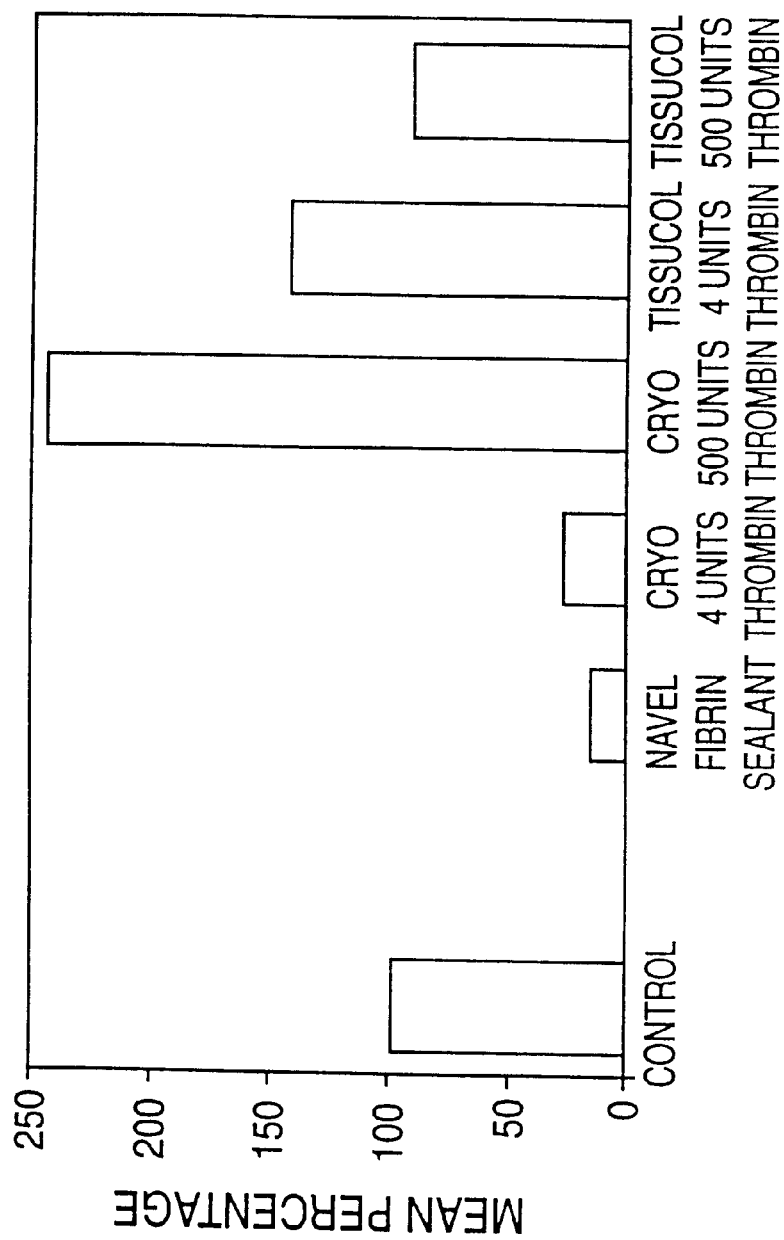
FIG. 10 Is a graphical representation of macroscopic PSA percentage volume.

Mean volumes of PSAs were 73.93 mm3 for the control group, 1130 mm3 for the Vivostat™ sealant treatment group, 21.06 and 179.98 mm3 for the CRYO treated groups with 4 and 500 units thrombin respectively and 106.12 and 69.42 mm3 for the Tissucol® treated groups with 4 and 500 units thrombin respectively, FIG. 9. Significant reduction in mean PSA volume compared to controls was seen with Vivostat™ sealant (P=0.001) and CRYO (P=0.0152) 4 units thrombin treated groups only:

Assuming that the control group demonstrated 100% PSA formation, the percentage volume of PSAs for each treatment was 15.28% Vivostat™ sealant, 28.49% CRYO (4 units thrombin), 243.46% CRYO (500 units thrombin), 143.55% Tissucol® (4 units thrombin) and 93.90% Tissucol® (500 units thrombin), FIG. 10.

Thus, the Vivostat fibrin I monomer based sealant demonstrated a superior prevention of PSAs in this model by providing a nearly 85% reduction in PSAs over the control and a significant improvement over the other sealants tested.

TABLE 8

Post Surgocal Incidence/Reduction

| Treatment | % PSA Incidence | % PSA Reduction |
|---|---|---|
| CONTROL | 100 | N/A |
| VIVOSTAT | 15.28 | 84.72 |
| CRYO + 4 units | 28.49 | 71.51 |
| CRYO + 500 units | 243.46 | −143.46 |
| Tissucol + 4 units | 143.55 | −43.55 |
| Tissucol + 500 units | 93.90 | 6.10 |

EXAMPLE 5

The aim of this example was to assess the ability of Vivostat™ Fibrin Monomer-Based Fibrin Sealant made from human blood (prepared as in Example 1) to reduce or prevent post surgical adhesions in a rat caecal abrasion model.

Experimental Procedure

Sixteen, female, Sprague Dawley rats were randomised into two groups. Each group received a standardized caecal and opposing peritoneal abrasion wounding which was either left untreated or sprayed with Vivostat™ Fibrin Sealant. The abrasions were then apposed with sutures. The animals were then allowed to recover and maintained in the animal unit for 14 days.

On day 14, the control and Vivostat™ Fibrin Sealant treated animals were euthanased and the experimental sites removed. The wounds were examined grossly, histopathologically and stereologically.

Results

The abrasion procedures resulted in an inadvertent perforation of the caecum in two animals (which was repaired using a purse string suture of 4/0 vicryl (Ethicon UK). The sites were still used for evaluation. All other surgical procedures were completed uneventfully.

There were no abnormal clinical signs observed and no mortalities.

The fibrin I solution concentrations used on the treated wounds ranged from 13.46 to 16.02 mg/ml. A mean volume of 0.79 ml Vivostat™ Fibrin Sealant was applied via the spray application to experimental sites.

Macroscopic examination of the wounds on day 14 showed adhesions in 8/8 control wounds and 0/8 Vivostat™ Fibrin Sealant treated wounds. All adhesions were dense, tenacious and fibrous.

Mean volume of post surgical adhesions measured stereologically was 89.91 mm$^3$ for control cases and 17.82 mm$^3$ for Vivostat™ Fibrin Sealant treated cases. There were fibrinous like connections, which were not considered to be adhesions, in the Vivostat™ Fibrin Sealant treated cases, but they were recorded as adhesion volumes for the purpose of analysis.

Conclusion

The mean volume of adhesions was significantly less (P<0.1) in the Vivostat™ Fibrin Sealant treated group compared to the control group. Vivostat™ Fibrin Sealant is an effective agent for the reduction of post-surgical adhesions when compared to controls in this rat caecal abrasion model.

EXAMPLE 6

This example is designed to evaluate the formation/prevention of PSAs in the stomach, colon and caecum of the pig by introducing a surgical injury to those sites similar to the rabbit uterine from model above. Pig models previously used to investigate PSAs demonstrate that pigs from PSAs in response to injury or trauma by identical pathogenesis to humans. In this example control (untreated/injured) animals were compared to those treated with of Vivostat™ Fibrin Monomer-Based Fibrin Sealant as prepared in Example 1, but wherein the sources were (a) human and (b) from the pig being treated, i.e., autologous sealant.

Pre-medication was administered using Ketamine (Ketalar-50 mg/ml ketamine hydrochloride. Supplied by Parke-Davis, Pontypool, Gwent.)(5 mgs/Kg) plus Xylazine (Rompun 2%-Xylazine hydrochloride 23.32 mg/ml (equivalent to 20 mg/ml xylazine) and 1 Mg/ml methyl 4-hydroxy-benzoate (preservative). Supplied by Bayer Plc., Animal Health Business Group, Bury St. Edmunds, Suffolk.)(1 mg/kg)) intramuscularly in the gluteous maximus muscle. At the operating suite, pigs were induced to and maintained at full anaesthesia with Halothane at 4% in oxygen and nitrous oxide delivered at 1.5 liters per minute and 0.5 liters respectively per minute via mask to the snout.

Once anaesthetised pigs were transferred to lay in the supine position on the operating table, where they were secured by soft tapes to each limb. A plastic ear tag bearing the unique pig identification number for the study was secured to one of the animals' ears. For each pig, the surgical site was shaved and scrubbed with chlorhexidine in alcohol followed by swabbing twice with iodine in alcohol. Sterile operative procedures were adhered to from this point on.

The animals were draped. Cutting diathermy and scissors were used to expose the spiral colon and the stomach through a midline laparotomy starting at the level of the distal xyphoid process of the sternum and extending distally 10–12 cms.

One area was selected on the lateral surface of the spiral colon or on the blunt end of the caecum and the mediolateral serosal aspect of the stomach such that these areas each laid naturally against the ipsilateral peritoneal wall. Areas were then selected on the ipsilateral peritoneal wall. As with the rabbit uterine horn abrasion model, each selected area was abraded, using a template and scraper, a standardised number of 12 scrapes which caused homogeneous punctate bleeding but not so far as to cause frank contiguous haemorrhage was performed.

A single throw suture (Ethibond 0.6 or similar) was placed at each end of the experimental site but outside of the abraded areas. These sutures passed only through the internal serosa of the peritoneum and then passed through the serosa at the respective ends of the apposed abraded areas on the stomach or colon. Sutures were tightened to bring the two apposed abraded areas close together but not in contact. For treated cases, human or porcine fibrin sealant was applied to the abraded areas (mean volume of 1.3 ml per experimental site), whereas no treatment was applied in control cases. Positional sutures were then tightened to bring the two abraded areas into close contact.

The laparotomy was closed in two layers, first with 2/0 Dexon Plus on an atraumatic half round needle for peritoneum and muscle layers, second with 2/0 Prolene or similar on half round cutting needle for skin. The first suture layer was of "transplant" longflow, over-under, non-interrupted crossed sutures, the second layer was of interrupted cruciate mattress sutures.

At 7 days post-surgery the animals were scarified and evaluated as follows. Animals were anaesthetised as for the surgical procedure. Laparotomy was reopened along the original incision, with experimental areas identified and macroscopic observations recorded and photographed.

The colon, caecum and stomach experimental sites, joined to the peritoneum by positional sutures at each end of the site, were resected. Euthanasia was achieved by high dose intravenous pentabarbitone (Expiral-Pentobarbitone sodium BP 200 mg/ml. Supplied by Sanofi Animal Health Ltd., Watford, Hertfordshire.) (150 mg/kg body weight)).

Resected tissues were trimmed of excess adipose tissue, pinned flat on stiff card, to retain a standard, lifelike tissue positional relationship, and immersion fixed in 10% neutral buffered formal saline for at least 24 hours at room temperature.

The table below summarizes the experiment.

| Treatment Group | Number of Animals | Injury Site | Number of Experimental Sites | Volume of Fibrin sealant Applied (ml) | Fibrin I Conc$^n$ (mg/ml) |
|---|---|---|---|---|---|
| Control | 3 | Stomach | 3 | N/A | N/A |
|  |  | Colon | 4 |  |  |
|  |  | Caecum | 2 |  |  |

-continued

| Treatment Group | Number of Animals | Injury Site | Number of Experimental Sites | Volume of Fibrin sealant Applied (ml) | Fibrin I Conc$^n$ (mg/ml) |
|---|---|---|---|---|---|
| | | | Total: 9 | | |
| Human fibrin sealant | 3 | Stomach Colon Caecum | 2 4 2 | 1.56 ± 0.06 | 18.01 ± 2.29 |
| | | | Total: 8 | | |
| Porcine fibrin sealant | 2 | Stomach Colon Caecum | 1 2 2 | 1.25 ± 0.05 | 19.45 ± 2.93 |
| | | | Total: 5 | | |

Results

All animals demonstrated general PSAs between the peritoneal suture line and underlying tissues: most frequently the omentum, ileum, caecum, spleen and liver respectively. All these PSAs were separated by blunt dissection and did not interfere with experimental sites.

All control experimental sites were adhered, many being quite severe. 5 out of the 8 sites treated with human fibrin sealant were clear of adhesions, with the remaining sites joined by either PSAs or fibrin sealant. 2 out of the 4 porcine fibrin sealant treated sites were identified as non-adhered with the other sites joined by either PSAs or fibrin sealant.

Figure 11:
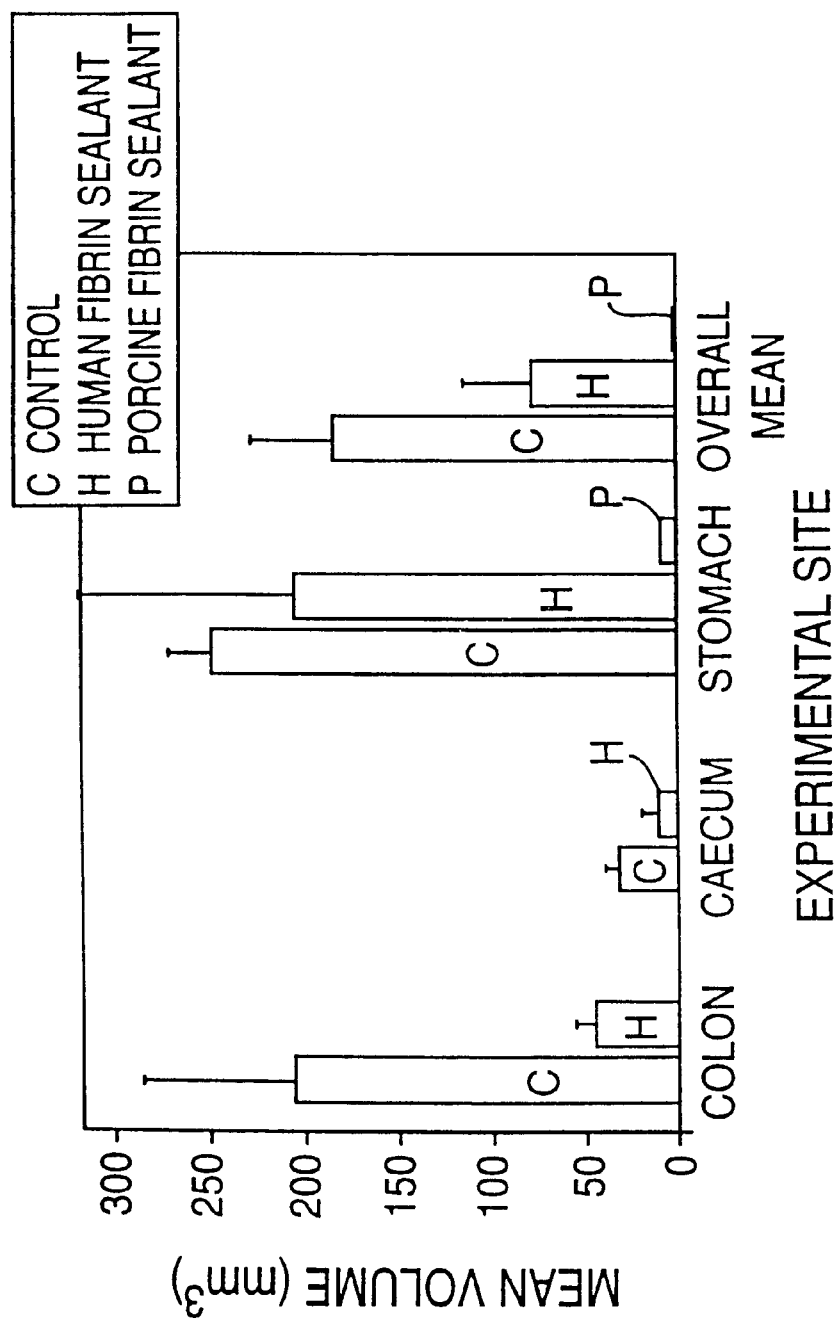
FIG. 11 Is a graphical representation of mean PSA volumes together with SEMs.

Mean volume of PSAs for the control group 207.25 mm$^3$ the colon, 31.33 mm$^3$ for the caecum and 248.11 mm$^3$ for the stomach with an overall mean of 181.78 mm$^3$. Human fibrin sealant treated group demonstrated mean volumes of 42.83 mm$^3$, 8.96 mm$^3$ and 204.47 mm$^3$ for the colon, caecum and stomach. respectively, with an overall volume of 74.77 mm$^3$. Whereas no PSAs were present in colon and caecum (FIG. 8.5) experimental sites treated wit porcine fibrin sealant, with 6.25 mm$^3$ for the stomach and a group mean of 1.27 mm$^3$, FIG. 11.

Figure 12:
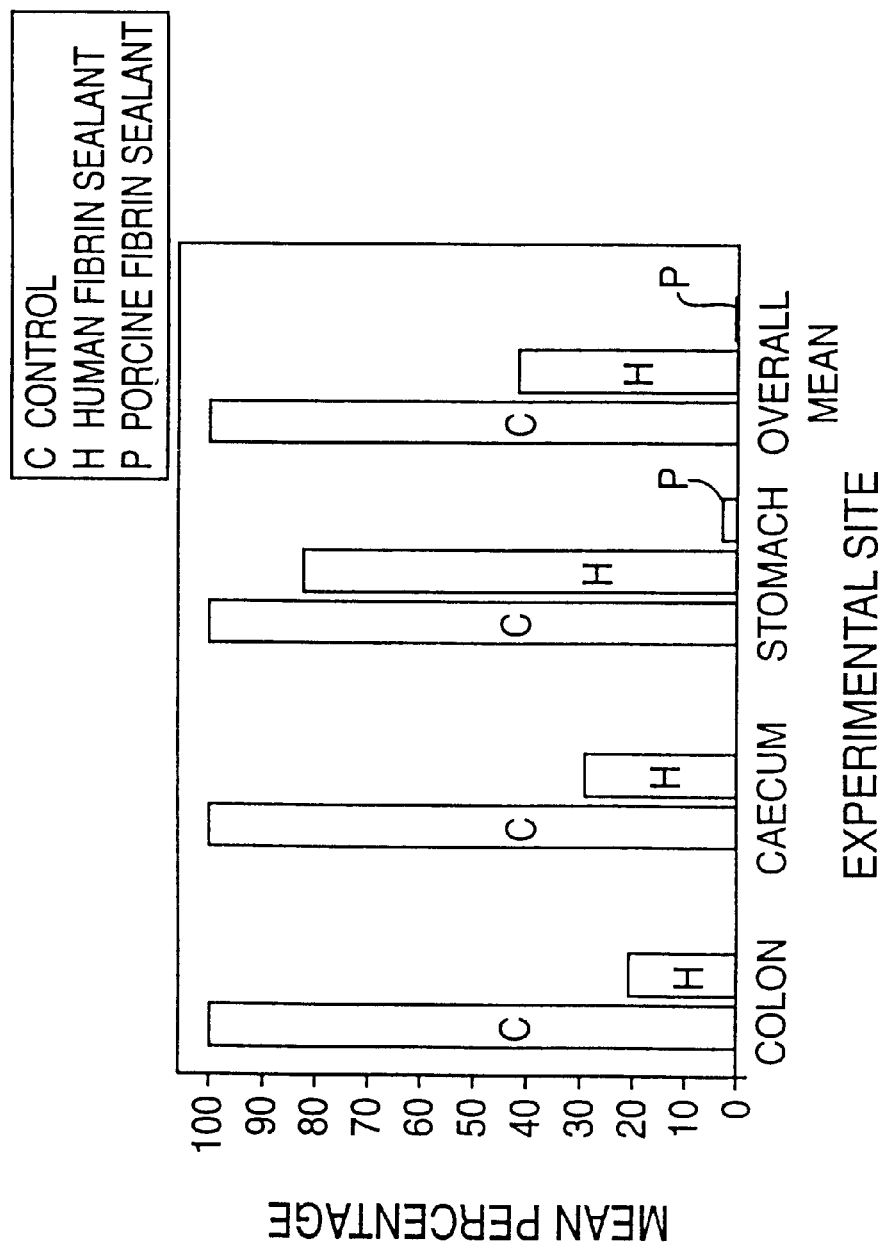
FIG. 12 Is a graphical representation of mean PSA percentages.

Assuming that the control group demonstrated 100% volume of PSA, reduction with human fibrin sealant was 79, 71 and 18% for the colon, caecum and stomach, respectively, with an overall reduction of 59%. Porcine fibrin sealant demonstrated 100% reduction for bath colon and caecum, 97% for the stomach and overall 99% reduction of PSAs compared to controls, FIG. 12.

What is claimed is:

1. A skin on the surface of a polymerized droplet of fibrin, wherein the skin comprises a layer of fibrin fibrils that are 10 to 20 times thinner than the fibrin fibrils at the center of the polymerized droplet.

2. The skin of claim 1, wherein the polymerized droplet of fibrin results from the polymerization of a polymerized fibrin monomer composition comprising at least 10 mg/ml of fibrin.

3. The skin of claim 1, wherein the polymerized droplet of fibrin results from the polymerization of a polymerized fibrin monomer composition comprising between 15 and 200 mg/ml of fibrin.

4. The skin of claim 1, wherein the polymerized droplet of fibrin results from the polymerization of a polymerized fibrin monomer composition comprising between 15 and 50 mg/ml of fibrin.

5. The skin of claim 1, wherein the polymerized droplet of fibrin results from the polymerization of a polymerized fibrin monomer composition comprising between 15 and 25 mg/ml of fibrin.

6. The skin of claim 1, wherein the polymerized droplet of fibrin has a diameter of between 5 and 250 μm.

7. The skin of claim 1, wherein the polymerized droplet of fibrin has a diameter of between 5 and 50 μm.

8. The skin of claim 1, wherein the fibrin fibrils comprise fibrin I polymer.

9. The skin of claim 8, wherein the fibrin I polymer is crosslinked.

10. The skin of claim 1, wherein the fibrin fibrils comprise fibrin ii polymer.

11. The skin of claim 10, wherein the fibrin II polymer is crosslinked.

* * * * *